United States Patent [19]
Bachmann et al.

[11] 3,971,968
[45] July 27, 1976

[54] ULTRAVIOLET RADIATION SOURCE INCLUDING TEMPERATURE CONTROL AND PRESSURE CONTROL OPERATING MEANS

[75] Inventors: Robert Bachmann, Dottingen; Pieter Bearda, Turgi; Walter Stoidl, Gebenstorf; Gerold Brandli, Aarau; Rudolf Rieder, Wettingen, all of Switzerland

[73] Assignee: BBC Brown Boveri & Company Limited, Baden, Switzerland

[22] Filed: Feb. 20, 1975

[21] Appl. No.: 551,425

[30] Foreign Application Priority Data

Mar. 4, 1974 Switzerland.......................... 2994/74
June 20, 1973 Switzerland.......................... 8456/74
Sept. 18, 1974 Switzerland.......................... 12672/74

[52] U.S. Cl................................. 315/108; 313/211; 313/220
[51] Int. Cl.² ................. H01J 61/067; H01J 61/30; H05B 41/36
[58] Field of Search .............. 315/108, 109; 313/220, 313/211

[56] References Cited
UNITED STATES PATENTS

| | | | |
|---|---|---|---|
| 2,165,709 | 7/1939 | Killian | 315/108 |
| 3,639,804 | 2/1972 | Hernqvist | 315/108 |

*Primary Examiner*—Palmer C. Demeo
*Attorney, Agent, or Firm*—Oblon, Fisher, Spivak, McClelland & Maier

[57] ABSTRACT

Apparatus for generating ultraviolet radiation of high spectral radiance whereby the radiation is produced in a discharge tube having a thermoemissive cathode and a discharge space and filled with mercury/argon by means of a wall-stabilized direct-current gas discharge at a mercury pressure $p_{Hg}$ of between $5 \times 10^{-3}$ and $5 \times 10^{-1}$ Torr and a current density $j$ of the discharge current I of between 1 and 25 A/cm². The discharge tube incorporates a pressure-equalizing space connecting the cathode space to the anode space whereby the sum of the volumes of the cathode space, anode space and pressure-equalizing space is greater than the volume of the discharge space. The pressure of the argon is maintained between 0.01 and 10 Torr. A first control element is provided which regulates the current density $j$ of the discharge current I to a constant value $j_0$ between 1 and 25 A/cm². A second control element is provided which regulates the pressure $p_{Hg}$ of the mercury to such a value that the yield $\eta$ of the line of wavelength 2537 A, i.e. the ratio of the spectral radiation power for the wavelength $\lambda = 2537$ A to the electrical power stored in the discharge, is at least 80% of the maximum yield $\eta_{max}$ for the chosen current density $j_0$.

30 Claims, 22 Drawing Figures

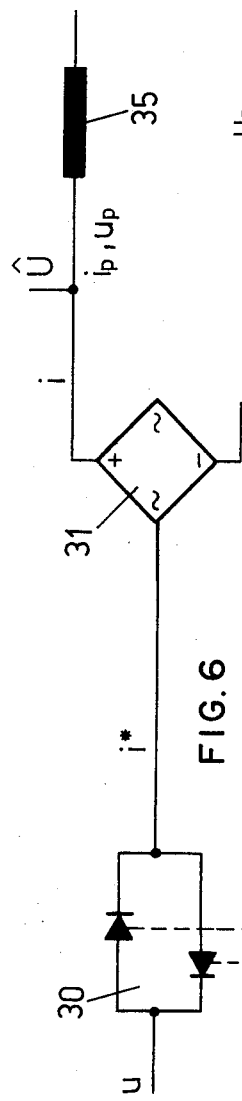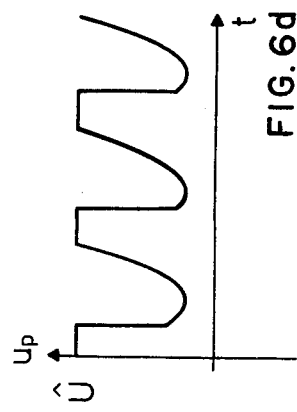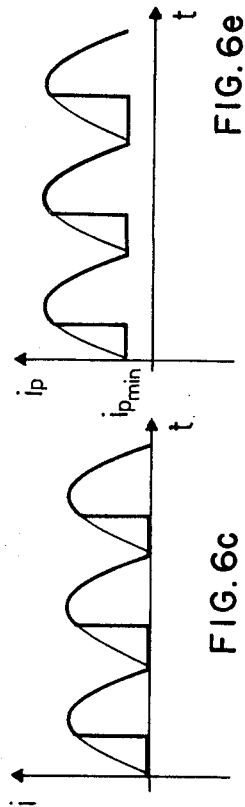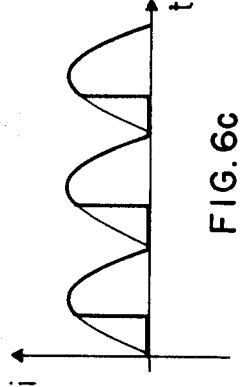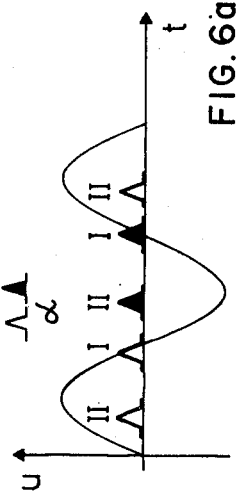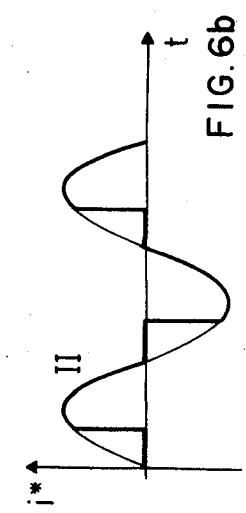
FIG. 6
FIG. 6a
FIG. 6b
FIG. 6c
FIG. 6d
FIG. 6e

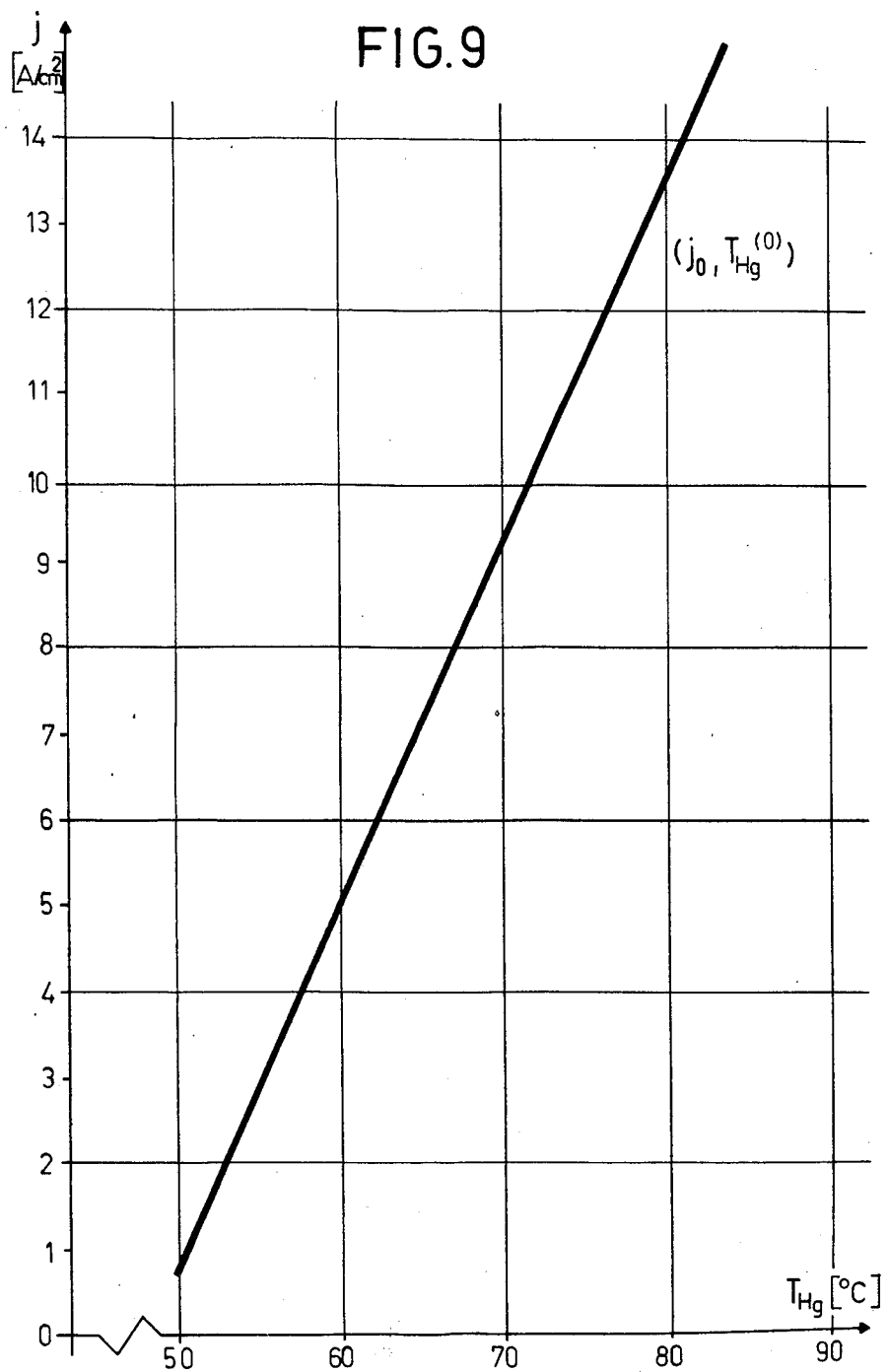

ULTRAVIOLET RADIATION SOURCE INCLUDING TEMPERATURE CONTROL AND PRESSURE CONTROL OPERATING MEANS

BACKGROUND OF THE INVENTION

1. Field of the Invention:

The invention concerns apparatus for generating ultraviolet radiation of high spectral radiance whereby the radiation is produced in a discharge tube having a thermoemissive cathode and a discharge space and filled with mercury/argon; by means of a wall-stabiized direct-current gas discharge at a mercury pressure $p_{Hg}$ of between $5 \times 10^{-3}$ and $5 \times 10^{-1}$ Torr and a current density $j$ of the discharge current I of between 1 and 25 A/cm².

2. Description of the Prior Art:

Such apparatus, termed a heavy-current low-pressure UV radiation source, is known for example from U.S. Pat. No. 3,679,928. The purpose of this known radiation source is to generate UV radiation with wavelengths below 2300 Angstrom (A) in particular to be used for stimulating photochemical reactions. This known radiation source, however, has so far not found acceptance in its intended market, probably, because it tends to unstable owing to plasma oscillation, and because its power consumption in relation to its UV output is too high to allow an economically acceptable useful life.

Light-current low-pressure UV radiation sources are well known from the field of fluorescent tube technology. Thus, from U.S. Pat. No. 3,117,248, for example, a UV radiation source with a mercury-gas discharge is known whereby the mercury vapor pumped from the anode to the cathode during the discharge can flow back to the anode through a duct joining the cathode space to the anode space. A similar source is known from U.S. Pat. No. 3,617,792 in which the return duct surrounds the discharge tube concentrically.

Finally, many different kinds of mercury heavy-current high-pressure and low-pressure burners for Raman spectroscopy are also known (e.g. Brandtmuller-Moser, Einfuhrung in die Raman-Spektroskpie, Steinkopf Verlag, 1962, pp. 144–159, 284–285, 298–303). However, these burners are designed almost without exception for longer wavelengths of more than 4000 A, and are not suitable for generating radiation in the far ultraviolet. Furthermore, the known burners are predominantly intended as laboratory equipment which cannot be used in technical or industrial applications.

SUMMARY OF THE INVENTION

An object of the invention is to create a UV radiation source of high spectral radiation, in particular for wavelength $\lambda = 2537$ A, which is well suited to industrial use from both technical and economic standpoints.

The foregoing and other objects are attained in accordance with one aspect of the present invention through the provision of apparatus of the kind described above wherein the discharge tube incorporates a pressure-equalizing space connecting the cathode space to the anode space whereby the sum of the volumes of the cathode space, anode space and pressure-equalizing space is greater than the volume of the discharge space, the pressure of the argon $p_{Ar}$ is between 0.01 and 10 Torr, a first control element is provided which regulates the current density $j$ of the discharge current I to a constant value $j_0$ between 1 and 25 A/cm², and a second control element is provided which regulates the pressure $p_{Hg}$ of the mercury to such a value that the yield $\eta$ of the line of wavelength 2537 A, i.e. the ratio of the spectral radiation power for the wavelength $\lambda = 2537$ A to the electrical power stored in the discharge, is at least 80% of the maximum yield $\eta_{max}$ for the chosen current density $j_0$.

The discharge space is preferably cylindrical and has a diameter D=4 to 20 mm.

With the apparatus of the invention it is possible for the first time to match the radiation power to the radiated substance by adjusting the discharge current density $j$, and at the same time, by suitably varying the mercury pressure, to maintain the UV yield in the region of its maximum, which is of very great importance not only for efficiency, but also for optimum life expectancy of the radiation source. The special configuration of the volumes of the discharge space and of the anode, cathode and pressure-equalizing spaces has the effect of preventing plasma oscillation and thus allows stable burning, together with uniform pressure of the discharge medium, which is determined solely by the coldest part of the system. As a result of the argon pressure of the invention, the lamp can be ignited without unacceptably high expense, while arc-through from the cathode to the anode is largely prevented by the pressure-equalizing space. The argon pressure in practice is generally between 0.01 and 0.10 Torr.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 6 shows the current storage unit. FIGS 6a, 6b, and 6c show the currents and voltages occuring in the current-storage unit.

FIG. 9 shows the relationship between the discharge current density $j_0$ and the temperature $T_{Hg}^{(0)}$ determining the mercury pressure which must be observed for optimum operation of the apparatus in accordance with the invention.

DETAILED DESCRIPTION OF THE PREFERRED EMBODIMENTS

Figure 1:
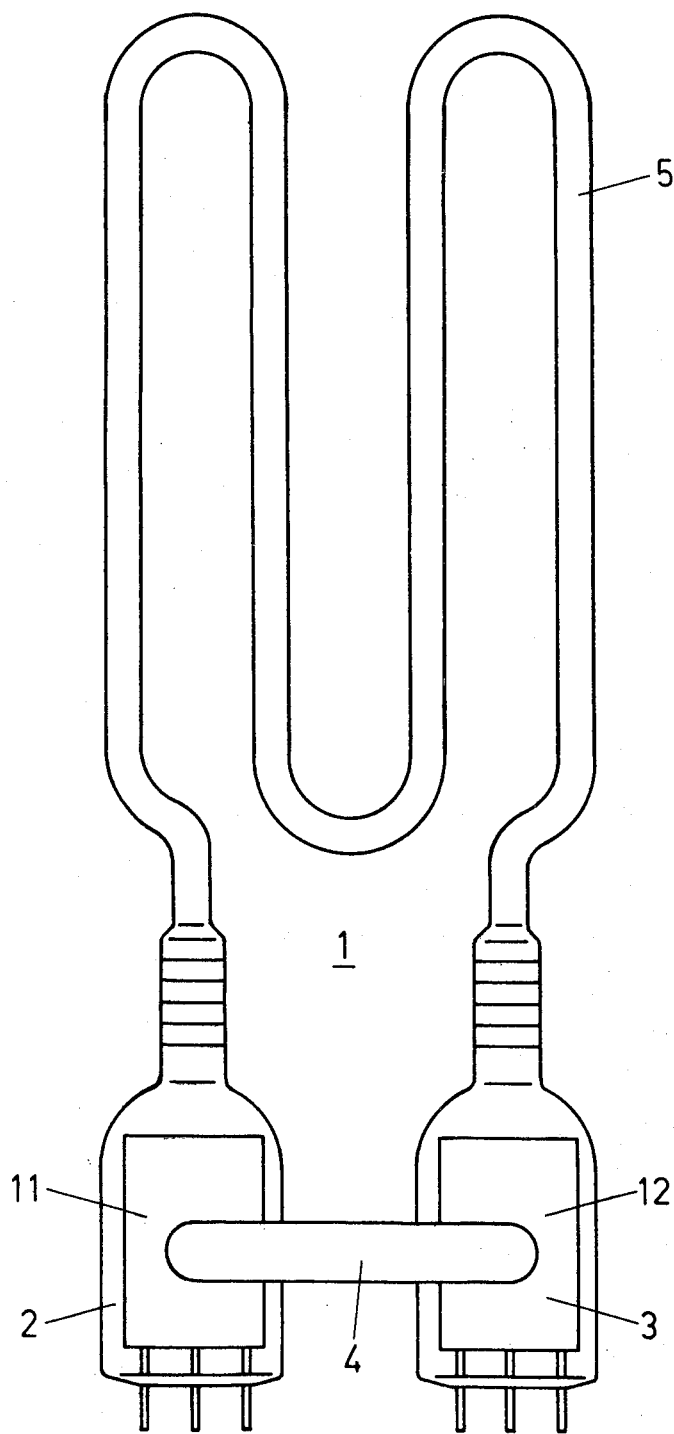
FIG. 1 shows a discharge tube with an M-shaped discharge space.

Referring now to the drawings, wherein like reference numerals designate identical or corresponding parts throughout the several views, and more particularly to FIG. 1 thereof, FIG. 1 shows a discharge tube 1 comprising a cathode space 2, an anode space 3, a pressure-equalizing space 4 connecting these two spaces, and an M-shaped discharge space 5.

Figure 2:
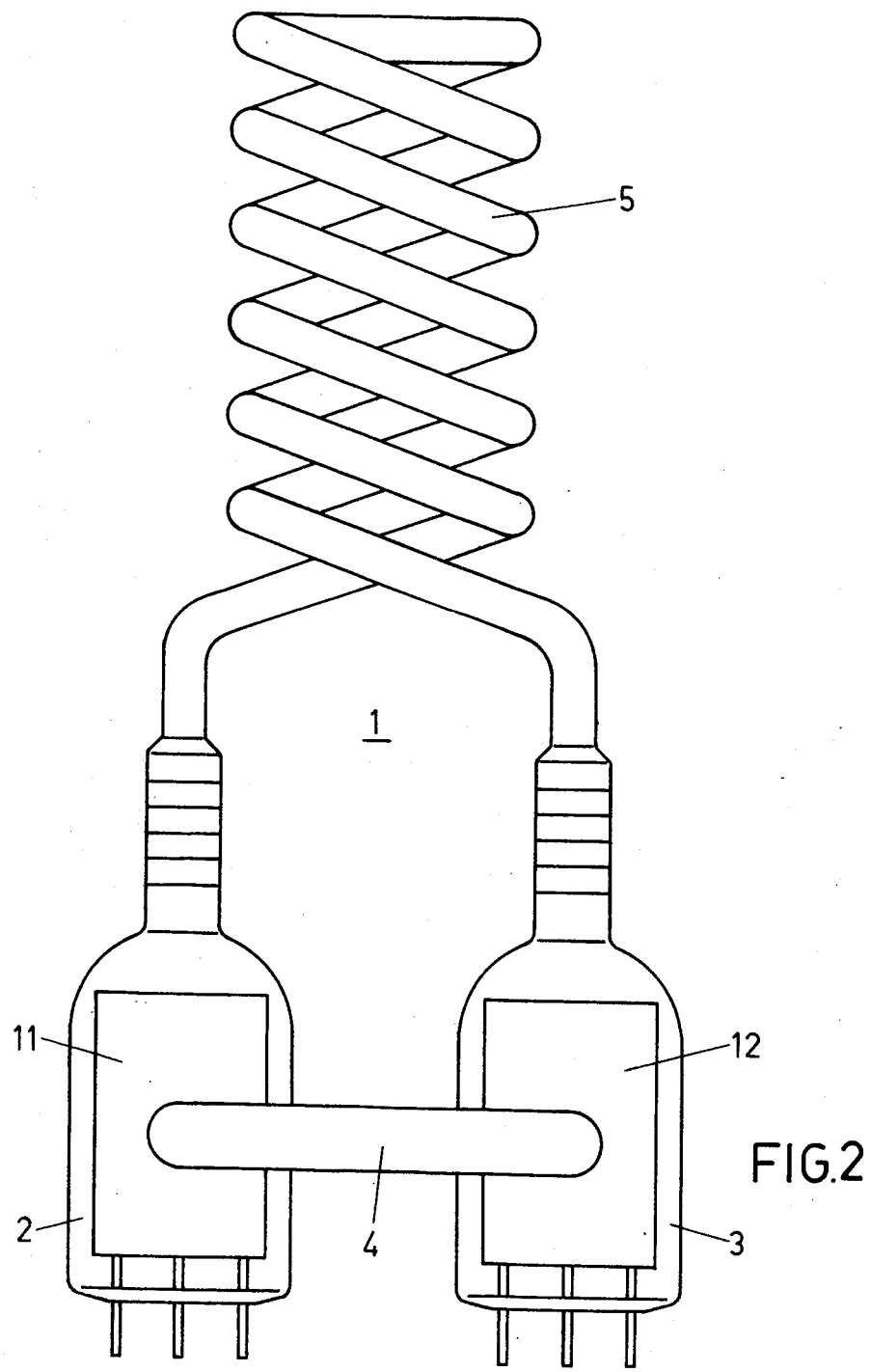
FIG. 2 shows a discharge tube with a helical discharge space.

FIG. 2 shows an alternative of the discharge space 1 depicted in FIG. 1, the discharge space 5 in this case being helical.

The discharge tube in FIG. 2 is used for radiating material located on the axis of the helix.

Figure 3:
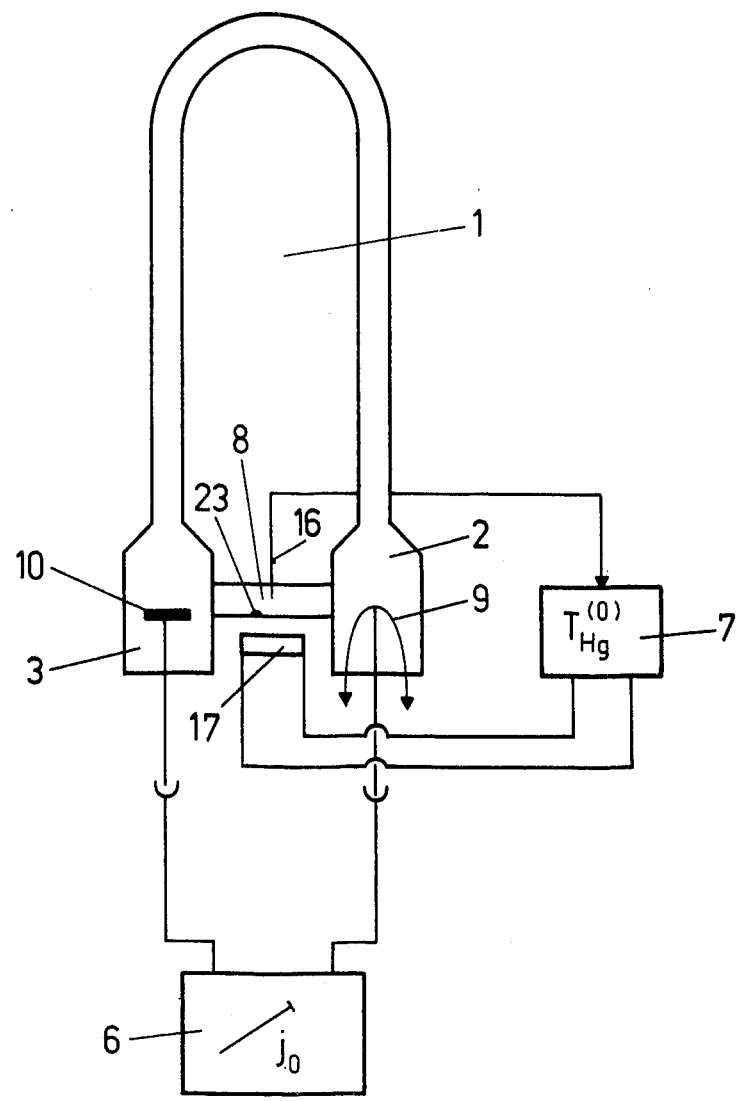
FIG. 3 shows a discharge tube with a U-shaped discharge space and control elements for adjusting the discharge current and the mercury pressure.
Figure 4:
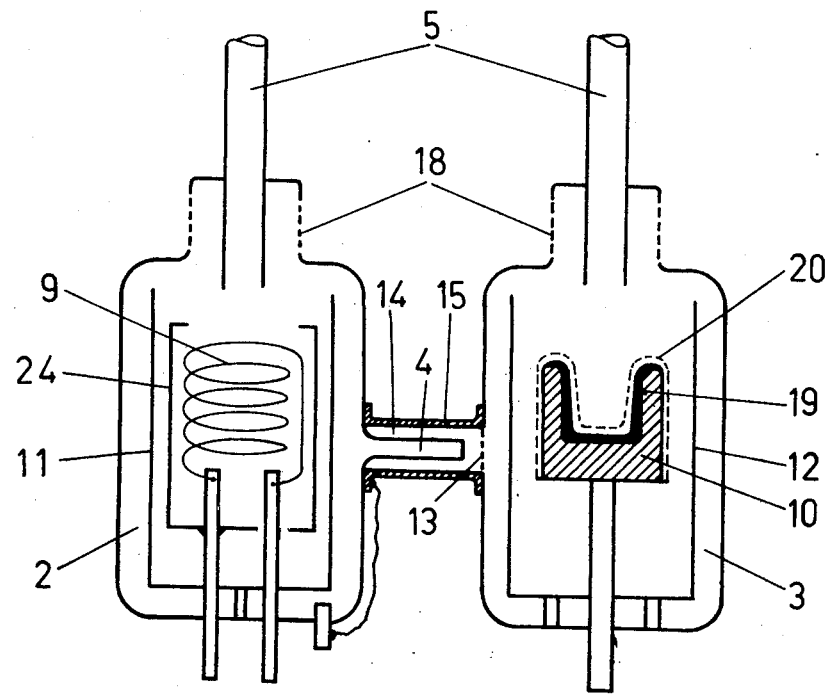
FIG. 4 shows the cathode, anode and pressure-equalizing space in detail.
Figure 4A:
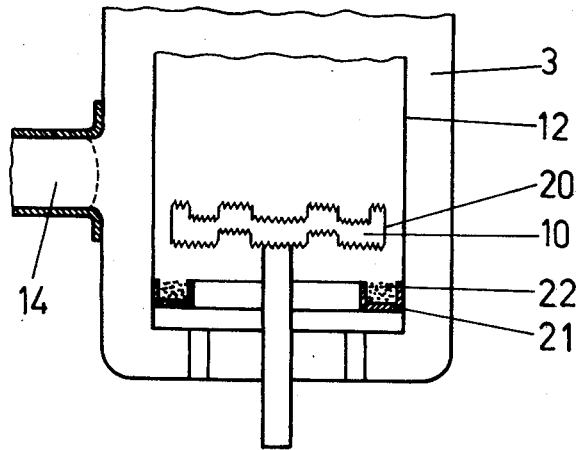
FIG. 4a shows an alternative anode space.

As shown in more detail in FIGS. 3, 4 and 4a, the discharge tube 1 has a cathode 9 in its cathode space 2 and an anode 10 in its anode space 3.

Cathode 9 is thermoemissive or also thermionic, i.e. it emits electrons when heated. It can be heated directly or indirectly. It comprises a BaO-coated strip of nickel mesh. It is surrounded by a can 24 which is open in the direction of the discharge space 5. The cathode 9 thus functions in the manner of a cylindrical cathode. The can 24 can also be of nickel. One end can be connected conductively to cathode 9.

In FIG. 4, the anode 10 is a graphite body which is cup-shaped to enlarge its surface area so as to improve cooling. Because the anode 10 is subjected to high-energy electron bombardment during the discharge, and thus becomes very hot, the graphite body is covered with a hard-carbon coating 19 of pyrographite. This is completely non-porous and prevents the anode from emitting foreign matter, or being sputtered, when heated. The pyrographite coating 19 is provided with a coating of zirconium 20. This not only improves the radiation capacity of the anode, but also acts as a very effective getter.

In FIG. 4a, the anode 10 is of solid molybdenum in the form of a plate. To enlarge the surface area and improve cooling, in particular due to radiation, the surface is provided with grooves, ribs or the like. Using molybdenum as the high-melting is especially convenient because molybdenum, in contrast to tungsten for instance, can be shaped more easily. The anode 10 of solid molybdenum can also be provided with a zirconium coating 20.

The discharge tube 1 is filled with argon at a pressure of between 0.01 and 0.1 Torr, and mercury. Whereas introducing the gaseous argon presents no problems, a mercury dispenser 22 is provided for putting in the mercury, which, of course, is liquid at room temperature. This dispenser comprises a metal channel 21 with a mercury/aluminum/zirconium compound which is stable at room temperature. The compound does not break down until heated to 900° C.

The mercury is then liberated and condenses on the coolest part 8 of the discharge tube 1, preferably in the pressure-equalizing space 4, in the form of mercury droplets 23 (FIG. 3). The zirconium/aluminum compound is retained as a getter.

Both the cathode 9 and the anode 10 are surrounded by hollow cylinders 11, 12 of nickel, for example. These hollow cylinders serve as thermal shields. So that no voltage drop occurs with respect to the corresponding electrode 9 or 10, which would give rise to sputtering, the hollow cylinders 11, 12 are mounted on an electrically insulating suspension so that their potential floats.

The discharge space 5 is cylindrical and has an inside diameter D of 4 to 20mm.

The invention is based to a large extent on the knowledge that for optimum operation of the UV radiation source of the invention, the mercury pressure $p_{Hg}$ must have very specific values $p_{Hg}^{(o)}$ for given values $j_o$ of the discharge current density. For the radiation source of the invention, this pressure $p_{Hg}^{(o)}$ is determined by the temperature $T_{Hg}^{(o)}$ of the coolest part 8 of the system, which is preferably in the pressure-equalizing space 4. With the apparatus of the invention, therefore, the first control element 6 for regulatng the discharge to a specified current density $j_o$ is supplemented by a second control element 7 which is fed from a temperature sensor 16, e.g. a thermistor, with the actual temperature of the coldest point 8, and then regulates the temperature of this point 8 to the desired temperature by means of a heating device 17. The heating device 17 can be a heating resistance, if appropriate, couple to a Peltier element, but can also be a fan which blows heated air to point 8 and the anode space 3.

In order to determine the correct mercury pressure $p_{Hg}^{(o)}$, or the corresponding temperature $T_{Hg}^{(o)}$, it is necessary to know the pattern of the yield $\eta$ of the line of wavelength 2357 A as a function of $p_{Hg}$ or $T_{Hg}$. This relationship is shown in FIG. 8c). According to this, with a discharge tube of length L = 170 cm (measured through the discharge space 5 from cathode 9 to anode 10) and a discharge space 5 of inside diameter D=10 mm, filled with argon at a pressure of $p_{Ar} = 0.05$ Torr, the maximum yield shifts from $T_{Hg}^{(o)} \approx 60°C$ when I = 4 A, to $T_{Hg}^{(o)} \approx 85°C$ when I = 12 A. Since, in accordance with the invention, $p_{Hg}$ is so regulated that the yield must be at least 80% of $\eta_{max}$, it follows from FIG. 8c) that $I_o = 4$ A gives a $T_{Hg}^{(o)} = 52°$ to 69°C, $I_o = 8$ A gives a $T_{Hg}^{(o)} = 61°$ to 86°C, and $I_o = 12$ A gives a $T_{Hg}^{(o)} = 72°$ to 96°C.

The rule for regulation of the mercury temperature $T_{Hg}^{(o)}$ in relation to the chosen discharge current density $j_o$ can be formulated in more concrete terms as follows:

$$T_{Hg}^{(o)} \text{ deg} = 2.4 \ \frac{\text{deg} \times \text{cm}^2}{A} j_o \ (A/cm^2) + 48 \ (\text{deg}).$$

This rule is shown for the second control element 7 by the straight line in FIG. 9, and is valid within the following limits:

$p_{Hg} = 10^{-2}$ to $4 \times 10^{-1}$ Torr, equivalent to $T_{Hg} = 45°$ to 100° C $p_{Ar} = 2 \times 10^{-2}$ to $8 \times 10^{-2}$ Torr $D = 8$ to 12 mm $j_o = 1$ to 16 A/cm²

When $T_{Hg}$ is regulated to the values of $T_{Hg}^{(o)}$ obtained with the equation given above, $\eta$ is at least very close to its maximum. However, since for practical reasons it is permissible to operate the radiation source of the invention also at 80% of $\eta_{max}$, deviations of ± 15% from the values of $T_{Hg}^{(o)}$ obtained with the equation are possible without going beyond the scope of the invention.

Figure 8A:
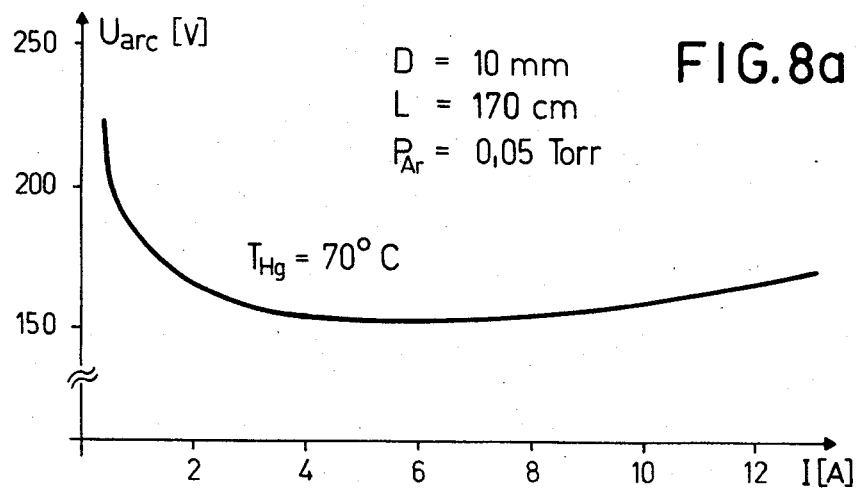
FIG. 8a shows the arc voltage $U_{arc}$ as a function of discharge current.
Figure 8B:
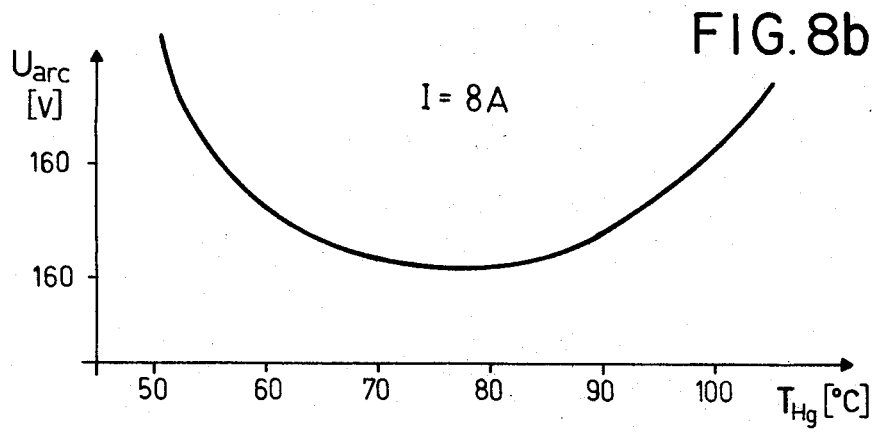
FIG. 8b shows the arc voltage $U_{arc}$ as a function of mercury temperature $T_{Hg}$.
Figure 8C:
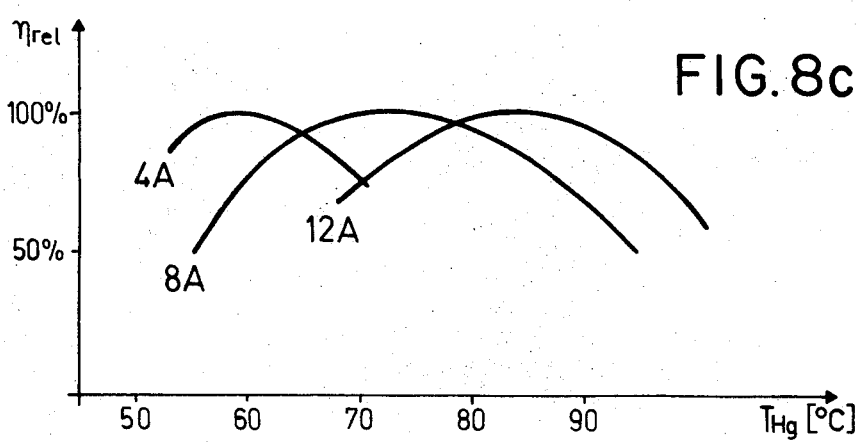
FIG. 8c shows the yield $\eta$ of the line of wavelength 2357A as a function of $T_{Hg}$.

FIG. 8a shows the arc voltage $U_{arc}$ as a function of discharge current I, and FIG. 8b as a function of mercury temperature $T_{Hg}$. From this it can be seen that in the case of a radiation source with parameters of the invention, the arc voltage cannot be used as either a measured variable or a controlled variable.

Although the pressure-equalizing space 4 is important for stabilizing the discharge, it also gives rise to the danger that the discharge will arc directly through the pressure-equalizing space 4. This danger increases with rising argon pressure $p_{Ar}$. To counteract this, three measures can be taken, either individually or preferably together.

The geometry of the pressure-equalizing space 4 is so chosen that the voltage required to strike an arc straight through the pressure-equalizing space 4 is as high as possible. One way of doing this is to make the diameter of pressure-equalizing space 4 as small as possible. On the other hand, the diameter must be sufficiently large to allow pressure equalization to take place between the electrode spaces 2 and 3. In these respects a form as shown in FIG. 4 has proved effective wherein the pressure-equalizing space 4 comprises a tube of diameter $d = 2$ to 4 mm contained within a tube 14 which acts only as a stable connection between the two electrode spaces 2 and 3. To raise the ignition voltage, the smaller tube can be oval or non-circular in some other way. (At this point it should be mentioned that electrode spaces 2 and 3, the tube of the pressure-equalizing space 4 and also that forming the mechanical link 14 are made of normal glass, and only the tube enclosing the discharge space 5 must be of quartz glass to allow transmission of the UV radiaton. As can be seen from FIG. 4, for example, the quartz tube is joined to the electrode spaces by means of a joint comprising glass rings fused together which have thermal expansion coefficients which approximate those of quartz and normal glass).

The electrical field distribution created by the electrically "floating" hollow cylinders 11 and 12 is influenced by internal measures. It has been found that the hollow cylinders 11 and 12 produce a field which focuses in towards the pressure-equalizing space 4. The field distribution is greatly improved by positioning an electrically insulated grid 13 at at least one of the entries to the pressure-equalizing space 4. In addition, the hollow cylinders 11, 12 themselves have the effect of impeding arc-through.

The electrical field distribution is influenced by external measures. A conductive coating 15, of silver, gold or graphite, for example, on tube 14, with a preferably negative electrical potential, e.g. of $-100$ V relative to cathode 9, has proved particularly effective. Here it is important that the coating should extend over the flange of tube 14 to the electrode spaces 2, 3. This almost completely eliminates the focussing field.

Nevertheless, the three measures stated above are not able to prevent with absolute certainty the occurrence of misfires through the pressure-equalizing space, especially if the discharge space is relatively long.

In a further important aspect of the invention, therefore, the passage of the gas in the pressure-equalizing space is so arranged that a part of its path proceeds from the cathode space to the anode space, and another part proceeds from the anode space to the cathode space. With a pressure-equalizing space of this form, the components of the mercury-vapor stream (Hg atoms, Hg ions and electrons), and if possible also of the argon, must be travelling along these sections move against the electrical potential present externally between cathode and anode, thus preventing arc-through.

Figure 4B:
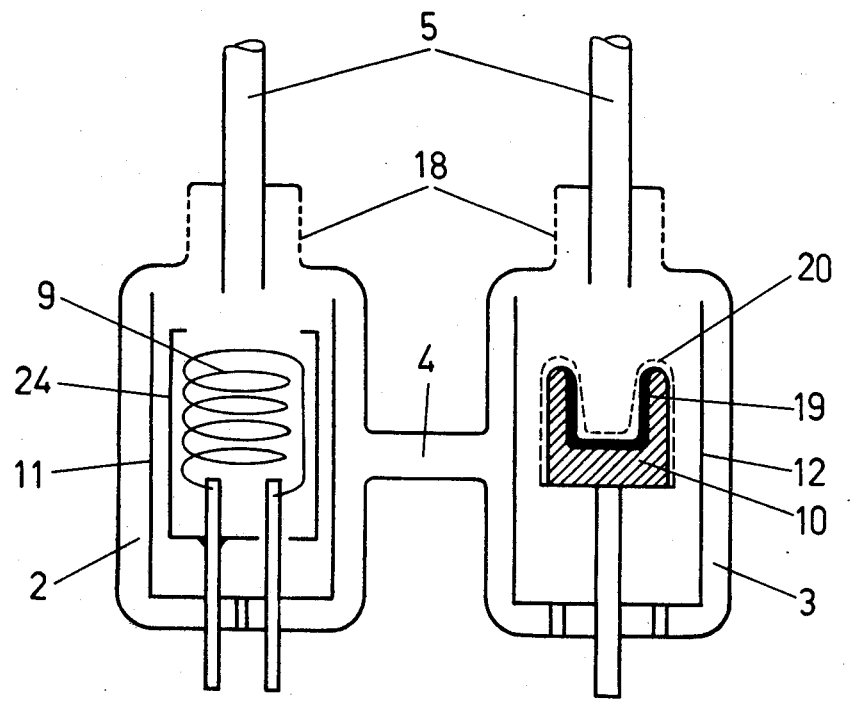
FIG. 4b shows the same view as FIG. 4, but without the special form of the pressure-equalizing space.

FIG. 4b again shows a view as in FIG. 4, but without the special configuration of the pressure-equalizing space 4. The pressure-equalizing space 4 of FIG. 4b is rather as shown in FIG. 4c or 4d.

Figure 4C:
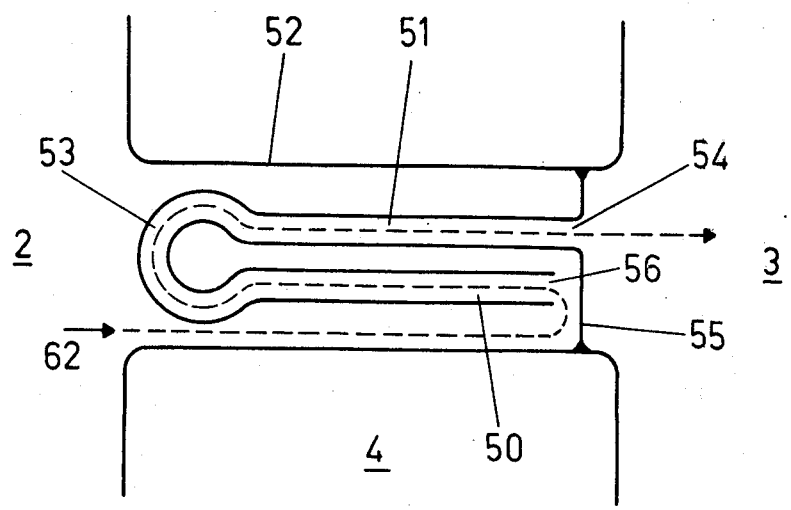
FIG. 4c shows a second special form of the pressure-equalizing space in accordance with the invention.

In FIG. 4c a straight tube 52, e.g. of diameter 16 mm, connects cathode space 2 with anode space 3. Within this tube 52 there is a U-shaped tube 53 with a diameter of some 2 to 8 mm, but typically 3.5 mm. The end 54 of one limb of this tube 53 is fused into a disc 55, which in turn is fused to tube 52 to form a tight seal and closes off tube 52 at the anode end. The turn of the U-tube 53 is located at the cathode end 2. The other limb of the U-tube 53 terminates in an opening 56 before the disc 44 at the anode end.

Figure 4D:
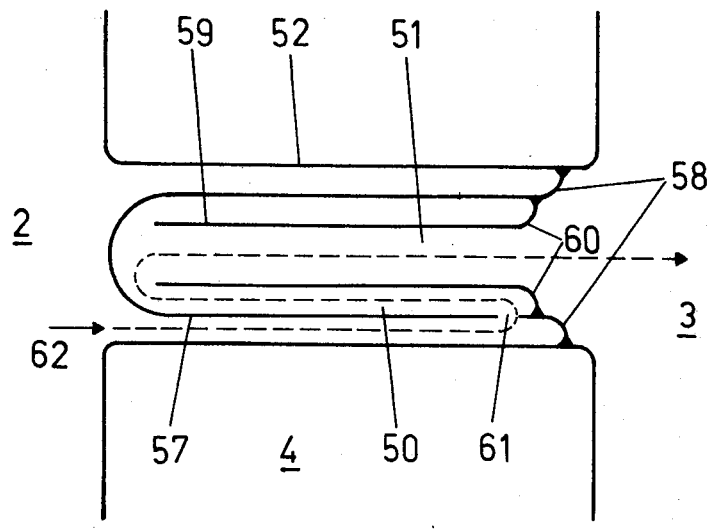
FIG. 4d shows a third special form of the pressure-equalizing space in accordance with the invention.

In FIG. 4d, a straight tube 52, of diameter 16 mm for example, connects the cathode space 2 to the anode space 3. This tube 52 contains a second, coaxial, straight tube 57, with a diameter of 10 mm for example, which is open at the anode end and its expanded lip 58 is fused to the inside wall of the first tube 52. This tube 57 is closed at the cathode end. Within this tube 57 there is then a third coaxial straight tube 59, e.g. 4mm in diameter, which is also open at the anode end, but its expanded lip 60 is fused to the second tube 57 to form a tight seal. This tube 59 is similarly open at the cathode end. The second tube 57 has at its anode end three openings 61, for example, of e.g. 3 mm diameter, which connect the space between the second (57) and first (52) tube to the space between second (57) and third (59) tubes.

In the versions shown in FIGS. 4c and 4d, pressure equalization of the mercury vapor pumped through pressure-equalizing space 5 from the anode 10 to the cathode 9 takes place along the broken line 62. With suitably chosen diameters, e.g. as stated above, the flow resistance is so small that pressure equalization takes place without any difficulty, even with small pressure differences, and the discharge is stable.

To prevent misfires it is an essential feature of the invention that a part 50 of the broken line 62 runs counter to the general direction 2 – 3. The electrical field along this portion 50 is then in the opposite direction to the electrons of the mercury vapor stream, especially until any space or surface charges have dispersed, and so prevents misfiring.

It is also most important that the positions of anode 10 and cathode 9 relative to the described structure of the pressure-equalizing space 4 should be as indicated in FIGS. 4c and 4d, i.e. the cathode 9 must be on the left, and the anode 10 on the right. If the arrangement is reversed, the certainty of preventing misfires is greatly reduced, possibly because electrons coming from the cathode 9 then pass into the tubes in such an unfavorable manner that surface charges build up on the inside of the tubes.

The configuration of the pressure-equalizing space 4 according to the invention allows an exclusively glass construction. Compared to the version described with reference to FIG. 4, there is no metallic conducting, electrically insulated grid 13, no coating 15 at an electric potential, and no circuit is required to apply the potential to this coating 15.

A particularly important advance, however, lies in the fact that with the pressure-equalizing space of the invention, UV radiation sources can be made with considerably longer discharge spaces 5 so that the voltage between anode and cathode is correspondingly higher.

Using a pressure-equalizing space in accordance with the invention, discharge tubes of the following dimensions have already been operated successfully:
Diameter of cathode space: 65 mm
Diameter of anode space: 65 mm
Height of cathode space: 100mm
Height of anode space: 100 mm
Diameter of outer pressure-equalizing tube: 16 mm
Length of pressure-equalizing space: 40 mm
Length of discharge space: 350 cm
Inside diameter of discharge space: 10 mm
Operating voltage: 300 V
Discharge current density: 10 A/cm$^2$ A further important aspect of the invention is the supply and control device for the discharge current, the "first control element" 6. Basically, this must satisfy the following requirements:

When the discharge tube 1 is fired with the discharge space cold ($T_{Hg}$ is low), the applied arc voltage must be a multiple of the operating arc voltage. When in operation, the current must be maintained at the prescribed constant value $I_0$. It must be possible to set different values of $I_0$. The current must not pass through zero, otherwise the radiation source will be extinguished. The control element must be inexpensive and dependable.

Figure 5:
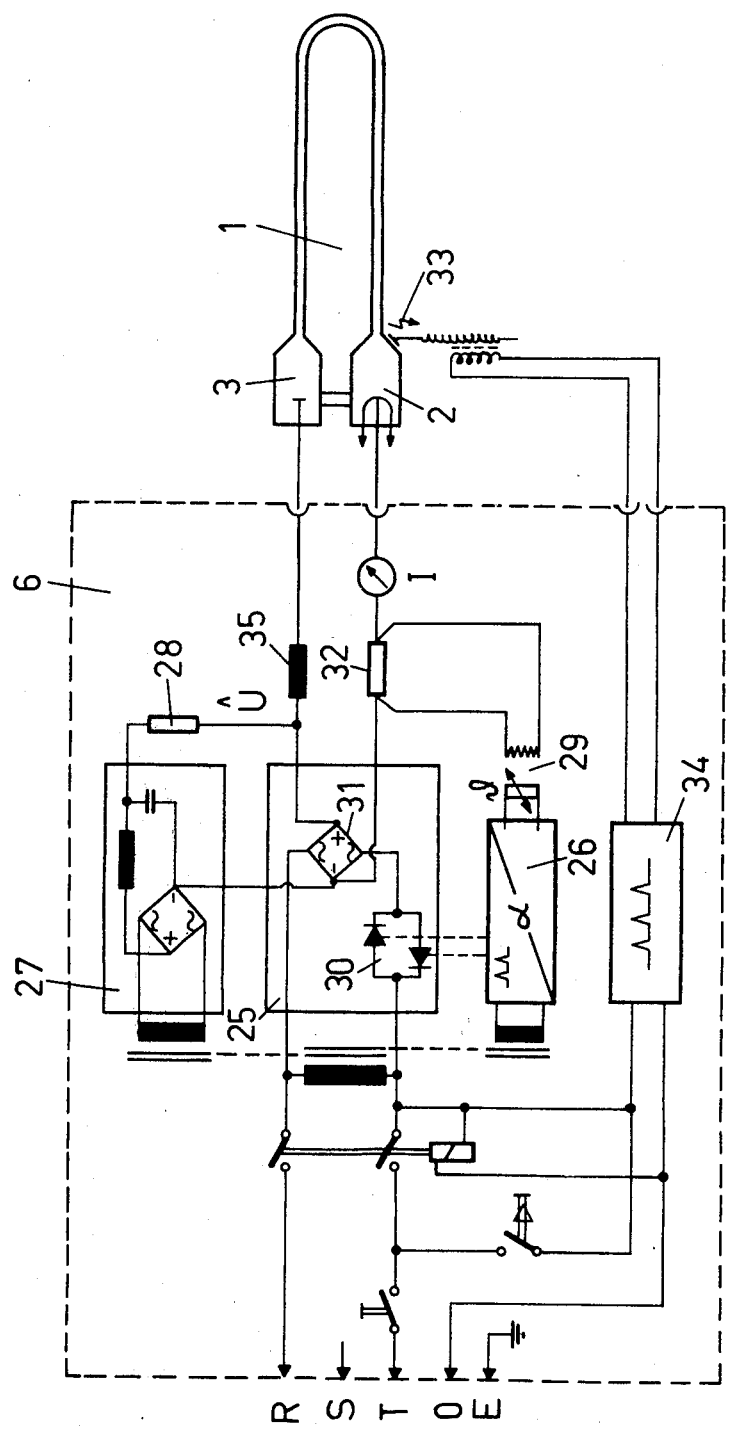
FIG. 5 shows a discharge tube with ignition and current-storage unit.

The control element 6 shown in FIG. 5 satisfies these requirements and constitutes a part of the invention.

The control element 6 incorporates a power unit 25 comprising two thyristors 30 connected in antiparallel and a bridge rectifier 31. The power unit 25 is connected to phases R and T, for example, of the three-phase power system. The firing angles $\alpha$ of the two thyristors are controlled by the control unit 26 described below with reference to FIG. 7. When $\alpha = 180°$, each passage of current is blocked by the two thyristors 30. When $\alpha = 0°$ the two phase voltages are allowed to pass through in full.

The input of control unit 26 is controlled by a heatable NTC resistor, the NTC unit 29, which is heated by the voltage across shunt 32. The current is thus regulated with a time lag, which is of particular advantage in view of the tendency of the system to oscillate (negative characteristic of the gas discharge).

A further advantage of this technique is that, prior to ignition, the NTC unit 29 can be preheated with an auxiliary voltage so that only a small current flows on ignition. When ignition occurs, this auxiliary voltage is then disconnected, and, as the NTC resistor cools, the discharge current slowly rises accordingly until the stabilized set value is reached. This prevents the current from overshooting on ignition.

To initiate the discharge, an auxiliary electrode 33 is provided on the outside of the cathode space 2 which is fed with a high voltage pulse from an ignition unit 34. Instead of the auxiliary electrode 33, an ignitor pin can be provided on the discharge tube 1.

The ignition voltage U, of 500 to 700 V, is provided from the d.c. voltage source 27, comprising a bridge rectifier, a choke and a capacitor. The d.c. voltage source 27 is connected in parallel to the power unit 25 by way of a high-value series resistor 28 ($R \approx 1$ to $5 k\Omega$). The effect of this is that when the value of the output current $i$ of the power unit 25 is zero, a small holding current $i_{pmin}$ continues to flow through the discharge tube 1 via the current-limiting series resistor 28 and prevents the discharge from extinguishing.

The currents and voltages of the power unit 25 are shown in FIG. 6.

The "white" pulses in the $u/t$ diagram control one of the thyristors 30, while the hatched pulses control the other.

The pulses I correspond to a firing angle $\alpha = 180°$. As can be seen, the current $i^*$, and accordingly also the current $i$, becomes zero.

The pulses II correspond to a firing angle $\alpha \approx 60°$. This gives rise to the heavily drawn curve for current $i^*$ and, beyond the bridge rectifier 31, the pulsating direct current $i$ and $_p$. Associated with the pulsating direct current $i_p$ is the pulsating d.c. voltage $u_p$ which fluctuates between the ignition voltage U and the arc voltage at maximum current. The pulsating direct current $i_p$, or the pulsating d.c. voltage $u_p$, is damped by means of a choke before they are fed into the discharge tube 1.

In normal operation the control system is so adjusted that the d.c. component of current $i$ together with the holding current $i_{pmin}$ provides a direct discharge current $I_0$ just sufficient to yield a discharge current density of $j_0$.

Figure 7:
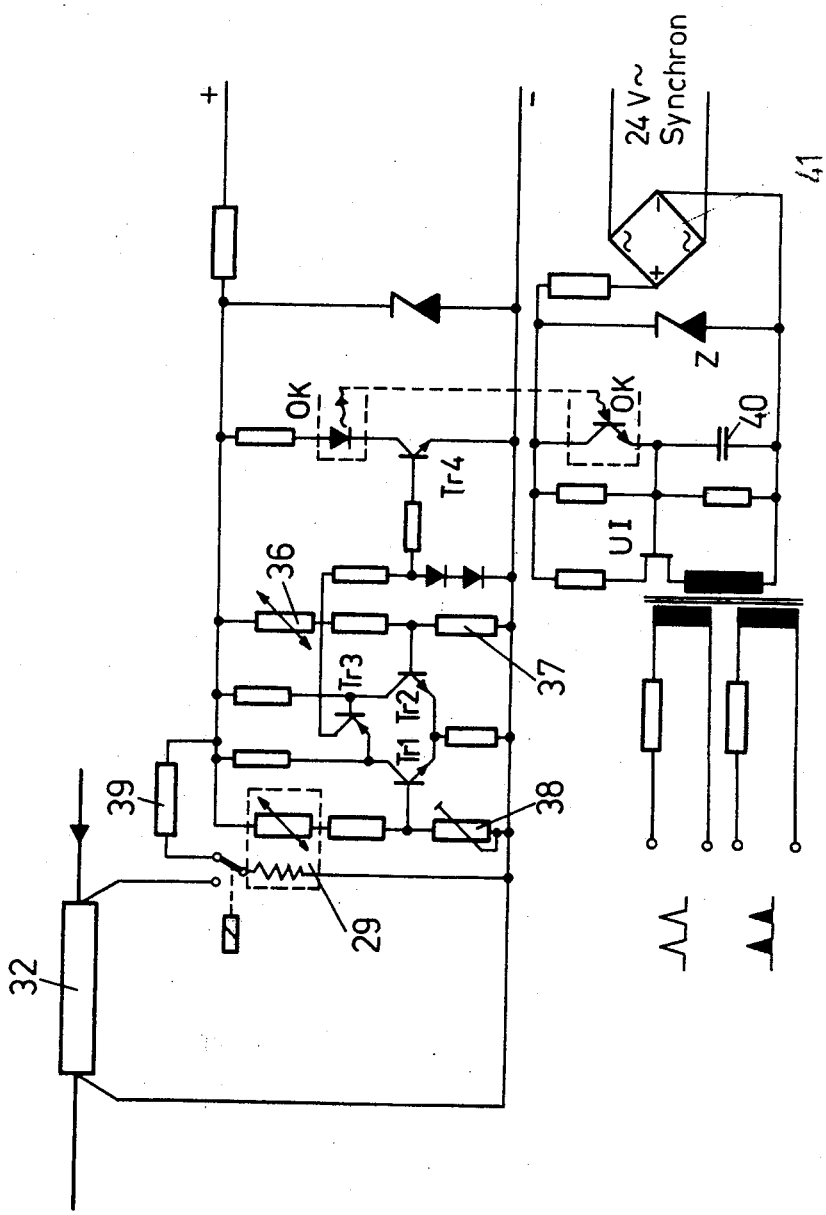
FIG. 7 shows the control device for generating the ignition pulses for the current-storage unit.

The control unit 26 shown in FIG. 7 functions essentially as follows:

The NTC resistor of the NTC unit 29 forms part of a bridge connection which also includes resistors 36, 37 and 38. 36 is an NTC resistor identical to the NTC resistor mentioned previously. 37 is a fixed resistor. The set value $I_0$ of the discharge current I is adjusted with resistor 38. The balancing leg of the bridge is formed by transistors Tr 1, Tr 2 and Tr 3. Transistor Tr 3 blocks all the time the bridge is balanced. With increasing imbalance, Tr 3 conducts more and more and causes an increasing current in transistor Tr 4.

In proportion to the current through Tr 4, the light-emitting diode of the optical coupler OK emits light of increasing intensity. This, in turn, further opens the transistor of the coupler OK.

The current flowing through the transistor of the optical coupler OK charges a capacitor 40, the voltage of which then opens a unijunction transistor UI when its threshold voltage is reached.

The transistor of the optical coupler OK and the primary part of the transformer T following the unijunction transistor UI are fed with a pulsating d.c. voltage produced by full-wave rectification in the bridge rectifier 41 and chopping to the Zener voltage of Zener diode Z. The bridge rectifier 41 is supplied with an a.c. voltage which is synchronous with the voltage feeding the antiparallel thyristors 30. As can be seen, pulses are produced on the secondary side of transformer T whenever the unijunction transistor UI is opened by capacitor 40. These pulses then control thyristors 30. The pulses will come sooner, the further the transistor of the optical coupler OK is opened. If the bridge 29 - 36 - 37 - 38 is balanced, the firing angle $\alpha$ of the pulses is such that the required direct discharge current $I_0$ is obtained. An imbalance in the bridge raises or lowers the value of $\alpha$.

The control unit described incorporates two notable features: First, so that the full current is not admitted to the discharge tube 1 on starting, which would give rise to unacceptable stability problems, the heating resistor of the NTC unit 29 is first connected to the starting resistor 39, and the NTC resistor is preheated. After the gas discharge has fired the system switches to the shunt 32 so that, since only a small discharge current is flowing for the time being, the NTC resistor cools down. This has the effect of shifting the ignition pulses at the output of the transformer T, at first only slowly, from the initial blocking position $\alpha \approx 180°$ to the subsequent operating position. Second, galvanically isolated control by way of the optical coupler OK is provided so that the base voltage of the transistor connected ahead of the capacitor 40 is not disturbed by the continuously changing emitter potential.

However, an arrangement of the radiation source as shown in FIGS. 1-4 and 4b is not suitable if the source has to be introduced into confined spaces, as is the case, for example, with packing machines for sterile liquid substances where the package is formed into a tube by shaping of the packed material.

This is made possible in another important alternative of the invention by arranging the two electrode spaces in series along the same axis so that there is a rear electrode space at the end of the whole apparatus, and a forward electrode space located between the rear electrode space and the discharge tube.

With such a configuration of the heavy-current low-pressure UV radiation source, whereby the whole apparatus thus consists essentially of the two electrode spaces, a tube for the discharge space and a second tube for the pressure-equalizing space, the cross-sectional area perpendicular to the longitudinal axis is a minimum.

Figure 10:
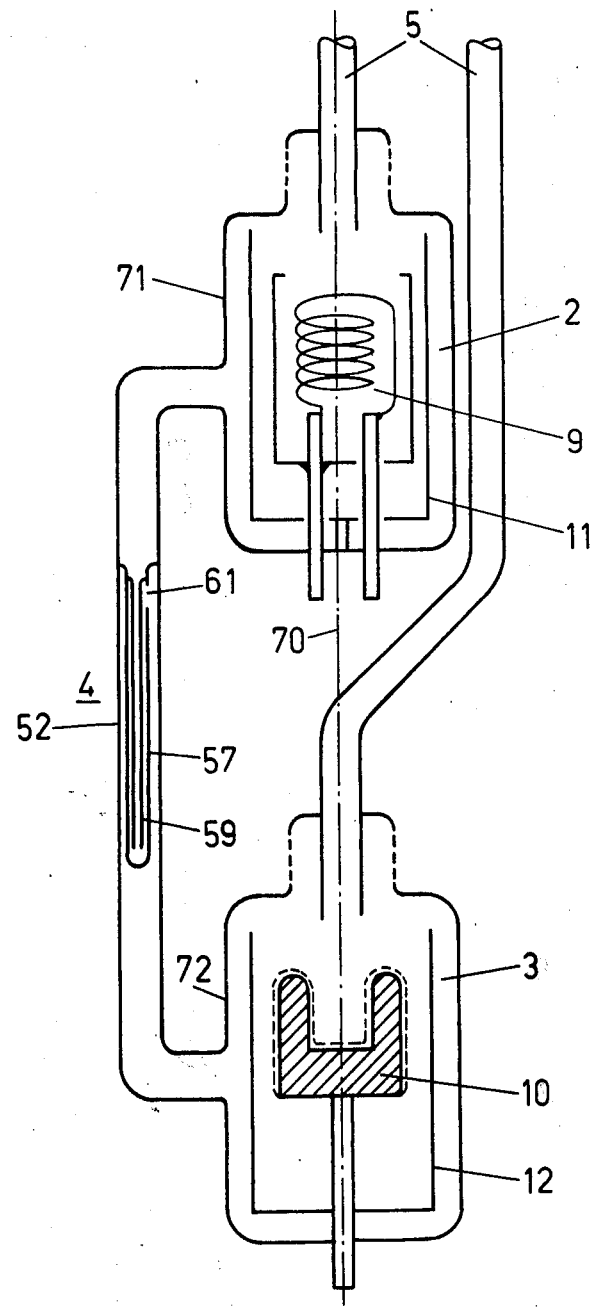
FIG. 10 shows a first form of the discharge tube with electrode spaces arranged in series.
Figure 11:
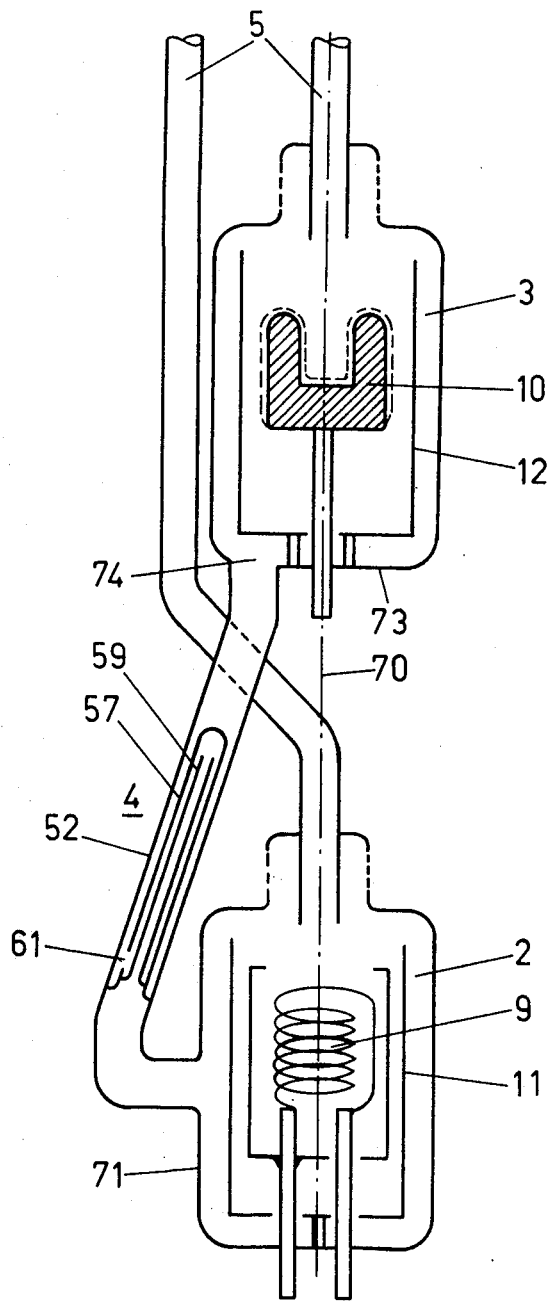
FIG. 11 shows a second form of the discharge tube with the electrode spaces arranged in series.

FIG. 10 and 11 show a heavy-current low-pressure UV radiation source comprising a cathode space 2, an anode space 3, a pressure-equalizing space 4 joining these two spaces, and a discharge tube 5.

In FIG. 10, the anode space 3 is located at the end of the whole apparatus, i.e. behind the cathode space 2 when viewed from the direction of the discharge tube 5, the two electrode spaces 2 and 3 on the same axis 70.

The pressure-equalizing space 4 is in each instance connected to the side wall 71, 72 of the cathode space 2 or anode space 3, respectively.

The pressure-equalizing space 4 is depicted as shown in FIG. 4d. In FIG. 11 the cathode space 2 is located at the end of the whole apparatus, i.e. behind the anode space 3 when viewed from the direction of the discharge tube 5, the two electrode spaces 2 and 3 again lying on the same axis 70.

In this version, the pressure-equalizing space 4 is connected to the base 73 of the forward electrode, i.e. the anode space 3, and to the side wall 71 of the rear electrode space, i.e. the cathode space 2.

The hollow metal cylinders 11 and 12, of nickel for example, surrounding the cathode 9 and anode 10, respectively, and serving essentially as thermal shields, are fixed in an electrically insulating mounting so that their potential floats.

These cylinders have openings where the electrode connections pass through. It is expedient that the openings in the base of the forward electrode space, e.g. 73, should not be opposite the aforementioned openings for the electrode connections, so that there is no danger of facilitating arc-through through the pressure-equalizing space 4.

It is understood that the scope of the invention is not exceeded if a UV radiation source of the kind considered, with suitably modified electrodes, is operated with alternating current instead of direct current, and each half-wave of the alternating current has the effect of a direct current as regards the gas discharge.

A final and important aspect of the invention lies in its use as apparatus, as described above, for high-speed dry in-situ cold sterilization, in particular of packaging materials for foodstuffs which cannot be sterilized by heating in the packed condition, e.g. milk products, or of liquids of sufficient UV transmissivity (e.g. water) or for surface sterilization of bulk materials and powders.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. Apparatus for generating ultraviolet radiation of high spectral radiance whereby the radiation is produced in a discharge tube having a thermoemissive cathode and a discharge space and filled with mercury-/argon by means of a wall-stabilized direct-current gas discharge at a mercury pressure $P_{Hg}$ of between $5 \times 10^{-1}$ Torr and a current density $j$ of the discharge current I of between 1 and 25 A/cm$^2$, comprising;

a discharge tube having a discharge space, a cathode space, and an anode space, and incorporating a pressure-equalizing space connecting the cathode space to the anode space so that the sum of the volume of the cathode space, anode space and pressure-equalizing space is greater than the volume of the discharge space, the pressure of the argon being between 0.01 and 10 Torr, first control means for regulating the current density $j$ of the discharge current I to a constant value $j_o$ between $l$ and 25 A/cm$^2$, and, second control means for regulating the pressure $p_{Hg}$ of the mercury to such a value that the yield $\eta$ of the line of wavelength 2537A, i.e. the ratio of the spectral radiation power for the wavelength $\lambda$ = 2537A to the electrical power stored in the discharge, is at least 80% of the maximum yield $\eta_{max}$ for the chosen current density $j_o$.

2. Apparatus as claimed in claim 1 in which for a mercury pressure $p_{Hg}$ between $10^{-2}$ and $4 \times 10^{-1}$ Torr, an argon pressure $p_{Ar}$ between $2 \times 10^{-2}$ and $8 \times 10^{-2}$ Torr, a diameter D of the discharge space between 8 and 12 mm, and a current density $j_o$ of the discharge current I between 1 and 16 A/cm$^2$, the second control means regulates the temperature $T_{Hg}$ of the coldest point of the discharge tube which determines the mercury pressure $p_{Hg}$ to a value of $T_{Hg}^{(o)} \pm 15\%$ which results from the equation:

$$T_{Hg}^{(o)} (\text{deg}) = 2.4 \ \frac{\text{deg} \times \text{cm}^2}{A} j_o(A/cm^2) + 48 \ (\text{deg}).$$

3. Apparatus as claimed in claim 1 in which the cathode and anode are each surrounded by a metallic conducting hollow cylinder mounted on an electrically insulating suspension.

4. Apparatus as claimed in claim 1 in which at least one of the two inlets into the pressure-equalizing space is terminated by a metallic conducting grid mounted on an electrically insulating suspension.

5. Apparatus as claimed in claim 1 whereby the pressure-equalizing space is contained within a tube between the electrode spaces provided at the ends of the limbs of the discharge space in which the outside of the tube containing the pressure-equalizing space is provided with a coating which is at an electrical potential and extends over the flange of the tube to the electrode spaces.

6. Apparatus as claimed in claim 5 in which the electrical potential of the coating with respect to the cathode is between 0 and −200 V.

7. Apparatus as claimed in claim 1 in which the anode is cup-shaped to enlarge its surface area and comprises a graphite body covered with a coating of pyrographite.

8. Apparatus as claimed in claim 1 in which the anode is provided with grooves and/or ribs to enlarge its surface area and comprises a solid metal body of molybdenum.

9. Apparatus as claimed in claim 7 in which a coating of zirconium is provided on the pyrographite coating or on the surface of the solid metal body.

10. Apparatus as claimed in claim 8 in which a coating of zirconium is provided on the pyrographite coating or on the surface of the solid metal body.

11. Apparatus as claimed in claim 1 in which a mercury dispenser is provided in the anode space.

12. Apparatus as claimed in claim 1 in which the first control means comprises a thyristor converter with phase-angle control as its power unit, a control unit which regulates the firing angle $\alpha$ of the thyristor converter and is driven by the discharge current I, and a d.c. voltage source in parallel with the power unit.

13. Apparatus as claimed in claim 12 in which the d.c. voltage source exhibits an output voltage U which is sufficient to ignite the unheated discharge tube and is connected to the anode of the discharge tube by a series resistor of such value that when the output current $i$ of the power unit is zero a holding current $i_{pmin}$ flows in the gas discharge.

14. Apparatus as claimed in claim 13, in which the output voltage U of the d.c. voltage source is 500 to 700 V and the series resistance is 1 to 5 k$\omega$.

15. Apparatus as claimed in claim 12 in which the control unit regulates the firing angle of the power unit so that the direct-current component of the pulsating current $i$ together with the holding current $i_{pmin}$ yields the value $I_0$ of the discharge current I which produces the selected value $j_0$ of the discharge current density.

16. Apparatus as claimed in claim 13 in which the control unit regulates the firing angle of the power unit so that the direct-current component of the pulsating current $i$ together with the holding current $i_{pmin}$ yields the value $I_0$ of the discharge current I which produces the selected value $j_0$ of the discharge current density.

17. Apparatus as claimed in claim 15 in which the input of the control unit is driven by a heatable temperature-sensitive resistor such as a NTC element which is heated by the discharge current I.

18. Apparatus as claimed in claim 17 in which before the discharge tube is started the NTC element is first connected across a starting resistor to an auxiliary voltage so that the power unit at first only produces a direct current smaller than 1A.

19. Apparatus as claimed in claim 17 in which the heatable temperature-sensitive resistor together with other resistors forms a bridge connection the balancing leg of which controls the current through the light-emitting diode of an optical coupler, the transistor of which is connected ahead of a capacitor whose voltage controls a unijunction transistor located in the primary circuit of a transformer supplied with a voltage which is synchronous with that feeding the thyristor converter of the power unit.

20. Apparatus as claimed in claim 1 in which the second control means has connected to its input a temperature sensor such as a thermistor located at the coldest point of the discharge tube such as the pressure-equalizing space, and to its output a heating device acting on the coldest point of the discharge tube.

21. Apparatus as claimed in claim 1 in which the passage of the gas in the pressure-equalizing space is so arranged that a part of its path proceeds from the cathode space to the anode space and another part of its path proceeds from the anode space to the cathode space.

22. Apparatus as claimed in claim 21 in which the pressure-equalizing space comprises a straight tube joining the cathode space to the anode space which contains a U-tube, of which the open end of one limb is inserted in a disc terminating the first tube at the anode end, its turn is located at the cathode end, and its other limb terminates in an opening before the disc at the anode end.

23. Apparatus as claimed in claim 21 in which the pressure-equalizing space comprises a straight tube joining the cathode space to the anode space which contains a second coaxial straight tube which is open at the anode end and has its expanded lip attached to the inside wall of the first tube, its cathode end being closed, the second tube containing a third coaxial straight tube which is open at the anode end and has its expanded lip attached to the inside wall of the second tube, its cathode end being open, the second tube having at its anode end at least one opening which connects the space between the first and the second tube to the space between the second and third tubes.

24. Apparatus as claimed in claim 21 in which all parts of the pressure-equalizing space are of glass.

25. Apparatus as claimed in claim 22 in which all parts of the pressure-equalizing space are of glass.

26. Apparatus as claimed in claim 23 in which all parts of the pressure-equalizing space are of glass.

27. Apparatus as claimed in claim 1 in which the two electrode spaces are arranged on the same axis so that there is a rear electrode space at the end of the whole apparatus and a forward electrode space between the rear electrode space and the discharge tube.

28. Apparatus as claimed in claim 27 in which the pressure-equalizing space is in each instance connected to the side wall of the two electrode spaces.

29. Apparatus as claimed in claim 27 in which the pressure-equalizing space is connected to the base of the forward electrode space and to the side wall of the rear electrode space.

30. Apparatus as claimed in claim 27 in which at least the electrode of the forward electrode space is surrounded by an electrically insulated hollow cylinder having at least one opening through which the electrode connection passes, this opening not being opposite the opening in the base of the forward electrode space.

* * * * *

UNITED STATES PATENT AND TRADEMARK OFFICE
CERTIFICATE OF CORRECTION

PATENT NO. : 3,971,968
DATED : July 27, 1976
INVENTOR(S) : ROBERT BACHMANN ET AL It is certified that error appears in the above-identified patent and that said Letters Patent are hereby corrected as shown below:

Column 10, line 27, after "5 x" insert $--10^{-3}$ and 5 x--.

Signed and Sealed this

First Day of November 1977

[SEAL]

Attest:

RUTH C. MASON
*Attesting Officer*

LUTRELLE F. PARKER
*Acting Commissioner of Patents and Trademarks*